(12) United States Patent
Guenther et al.

(10) Patent No.: US 10,722,639 B2
(45) Date of Patent: Jul. 28, 2020

(54) METHOD OF REMOVING BLOOD FROM AN EXTRACORPOREAL BLOOD CIRCUIT, TREATMENT APPARATUS, AND TUBE SYSTEM

(71) Applicant: Fresenius Medical Care Deutschland GmbH, Bad Homburg (DE)

(72) Inventors: Goetz Guenther, Oberusel (DE); Joachim Manke, Loehnberg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 470 days.

(21) Appl. No.: 15/418,187

(22) Filed: Jan. 27, 2017

(65) Prior Publication Data

US 2017/0173250 A1  Jun. 22, 2017

Related U.S. Application Data

(63) Continuation of application No. 12/765,928, filed on Apr. 23, 2010, now Pat. No. 9,592,332.

(Continued)

(30) Foreign Application Priority Data

Apr. 23, 2009  (DE) .................. 10 2009 018 664
Jun. 10, 2009  (DE) .................. 10 2009 024 606

(51) Int. Cl.
*A61M 1/36* (2006.01)
*A61M 1/34* (2006.01)

(52) U.S. Cl.
CPC .......... *A61M 1/3646* (2014.02); *A61M 1/342* (2013.01); *A61M 1/3434* (2014.02);
(Continued)

(58) Field of Classification Search
CPC .............. A61M 1/3434; A61M 1/3437; A61M 1/3644; A61M 1/342; A61M 1/3626; A61M 1/3643; A61M 1/3653; A61M 1/3655
See application file for complete search history.

(56) References Cited

U.S. PATENT DOCUMENTS 4,493,693 A   1/1985 Bilstad et al.
4,552,721 A  11/1985 Fentress et al.
(Continued)

FOREIGN PATENT DOCUMENTS

DE   19605260   11/1996
DE   69428220    6/2002
(Continued)

OTHER PUBLICATIONS

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators 2004, ISBN 1-56020-210-9; abstract; p. vi; p. 50, section 107.1.2.
(Continued)

*Primary Examiner* — Ariana Zimbouski
(74) *Attorney, Agent, or Firm* — Fish & Richardson P.C.

(57) ABSTRACT

The present invention relates to a method of removing blood from an extracorporeal blood circuit following termination of a blood treatment session, wherein blood is concurrently removed both from an arterial conduit portion and from a venous conduit portion of the extracorporeal blood circuit. It further relates to a method for recognizing and/or eliminating air inclusions in or from an extracorporeal blood circuit and a treatment apparatus as well as a tube system.

18 Claims, 2 Drawing Sheets

Related U.S. Application Data

(60) Provisional application No. 61/185,651, filed on Jun. 10, 2009.

(52) U.S. Cl.
CPC ........ *A61M 1/3437* (2014.02); *A61M 1/3626* (2013.01); *A61M 1/3643* (2013.01); *A61M 1/3644* (2014.02); *A61M 1/3653* (2013.01); *A61M 1/3655* (2013.01); *A61M 2205/12* (2013.01); *A61M 2205/60* (2013.01)

(56) References Cited

U.S. PATENT DOCUMENTS

| | | | |
|---|---|---|---|
| 4,898,675 A * | 2/1990 | Lavender | A61M 1/3496 |
| | | | 210/321.65 |
| 5,690,831 A | 11/1997 | Kenley et al. | |
| 5,776,345 A | 7/1998 | Truitt et al. | |
| 5,788,099 A | 8/1998 | Treu et al. | |
| 2002/0023880 A1 | 2/2002 | Pedrini et al. | |
| 2002/0147423 A1 * | 10/2002 | Burbank | A61M 1/282 |
| | | | 604/6.16 |
| 2004/0168969 A1 | 9/2004 | Sternby et al. | |
| 2005/0065459 A1 | 3/2005 | Zhang et al. | |
| 2005/0185772 A1 | 8/2005 | Chen et al. | |
| 2006/0084906 A1 | 4/2006 | Burbank et al. | |
| 2006/0254982 A1 | 11/2006 | Kopperschmidt | |
| 2007/0196320 A1 | 8/2007 | Yasin | |
| 2008/0027368 A1 * | 1/2008 | Kollar | A61M 1/3621 |
| | | | 604/6.14 |
| 2008/0149551 A1 | 6/2008 | Brugger et al. | |
| 2009/0032469 A1 * | 2/2009 | Panzani | B01D 29/21 |
| | | | 210/646 |
| 2010/0087772 A1 | 4/2010 | Gronau et al. | |
| 2011/0048101 A1 | 3/2011 | Heide et al. | |

FOREIGN PATENT DOCUMENTS

| | | |
|---|---|---|
| DE | 102 45 619 | 3/2004 |
| DE | 10 2008 010 948 | 9/2009 |
| DE | 10 2009 008346.4 | 8/2010 |
| DE | 10 2009 008664.6 | 8/2010 |
| DE | 10 2009 012632.5 | 9/2010 |
| DE | 10 2009 024468.9 | 12/2010 |
| EP | 1 872 814 | 1/2008 |
| EP | 2 218 803 | 8/2010 |
| EP | 1 952 832 | 12/2014 |
| WO | 2008/028579 | 3/2008 |
| WO | 2010/102784 | 9/2010 |

OTHER PUBLICATIONS

International Search Report from PCT/EP2010/002322 dated Jul. 28, 2010.

\* cited by examiner

METHOD OF REMOVING BLOOD FROM AN EXTRACORPOREAL BLOOD CIRCUIT, TREATMENT APPARATUS, AND TUBE SYSTEM

CROSS REFERENCE TO RELATED APPLICATIONS

This application is a continuation application of and claims priority to U.S. patent application Ser. No. 12/765,928, filed Apr. 23, 2010, which claims the benefit of U.S. Provisional Application No. 61/185,651 filed Jun. 10, 2009, and claims priority to German Patent Application No. 10 2009 024 606.1 filed Jun. 10, 2009 and German Patent Application No. 10 2009018 664.6 filed Apr. 23, 2009, all of which are herein incorporated by reference in their entirety.

FIELD OF INVENTION

The present invention relates to a method of removing blood from an extracorporeal blood circuit and a method for recognizing and/or eliminating air inclusions in or from an extracorporeal blood circuit. It further relates to a treatment apparatus, as well as a tube system.

BACKGROUND OF THE INVENTION

In extracorporeal blood treatment, the recognition and elimination of inclusions of gas or air possibly existing in an extracorporeal blood circuit used for the blood treatment is highly relevant.

Extracorporeal blood circuits typically are one-way articles and are disposed after use. Here, it may be advantageous for various reasons to remove liquids from the extracorporeal blood circuit following termination of a blood treatment session. These reasons include aspects of hygiene and the costs for disposal of the used extracorporeal blood circuit.

SUMMARY OF THE INVENTION

It is an object of the present invention to specify another method of removing blood from an extracorporeal blood circuit following termination of a blood treatment session. Furthermore, it is intended to specify a method for recognizing and/or eliminating air present inside an extracorporeal blood circuit.

A "blood treatment session" as presently discussed may include, for example, a treatment by means of hemodialysis, hemofiltration, hemodiafiltration, and/or cell separation method. It may be directed to the cleansing or purification of blood. In order to perform such a blood treatment, a suitable treatment apparatus is used.

In use, a "treatment apparatus" suited for performing the method of the invention comprises at least one extracorporeal blood circuit or a reception means for such an extracorporeal blood circuit, at least one blood pump, as well as at least a second conveying means.

An "extracorporeal blood circuit" comprises at least one arterial conduit portion and at least one venous conduit portion. Each one of these conduit portions includes a conduit interior.

The extracorporeal blood circuit may be suited for being connected to a patient's vascular system. The extracorporeal blood circuit may, however, also be one which conducts blood extracorporeally during the treatment of the patient while, however, not being connected to the patient's vascular system.

A "patient's vascular system" should here be understood to be the patient's blood circulation in the sense of an anatomical structure including, i. a., fistulae, shunts or grafts applied post-partum, furthermore arterial and venous conduit structures of the body, and the like.

The expression "blood pump" should be understood as a conveying means that is suited and intended (hereinbelow used synonymously with "configured") for conveying blood in the extracorporeal blood circuit.

A "patient" within the meaning of the present invention may be a human or an animal.

A "second conveying means" is suited and intended for introducing at least one substitute liquid into the extracorporeal blood circuit.

A "substitute liquid" may, for example, be any substituate liquid customarily used in a blood treatment. In a preferred manner, the substitute liquid is a solution that was already used during the blood treatment session and thus was already integrated in, or may be introduced into the extracorporeal blood circuit via a fluid connection. It may preferably be an isotonic saline solution such as, e.g., a 0.9% NaCl solution. The substitute liquid may, for example, also be understood, e.g., to be a medicament introduced by means of a perfusor via an addition site.

Irrespective of its name, the substitute liquid may in accordance with the invention also be understood to be a fluid other than a liquid, the use of which is equally applicable in accordance with the invention.

The method of the invention includes the step of introducing or feeding substitute liquid into the extracorporeal blood circuit, preferably by operating the second conveying means.

The substitute liquid introduced or fed into the extracorporeal blood circuit may be conveyed through the extracorporeal blood circuit by operating the blood pump and/or the second conveying means.

By means of the substitute liquid conveyed in the extracorporeal blood circuit, it is possible to concurrently displace the blood of the patient that is present in the extracorporeal blood circuit after the blood treatment session, both from the arterial conduit portion and also from the venous conduit portion of the extracorporeal blood circuit.

The expression "concurrently" as presently used means that both the conveyance of blood from the arterial conduit portion and also the conveyance of blood from the venous conduit portion may take place at one and the same point of time x and/or during one and the same time period y.

In accordance with the invention, "concurrently" may be understood in the meanings of "simultaneously" or "at the same moment."

"Concurrent displacement" of blood both from the arterial conduit portion and also from the venous conduit portion of the extracorporeal blood circuit means that the blood is removed from the extracorporeal blood circuit out of both conduit portions of the extracorporeal blood circuit by means of the substitute liquid conveyed in the extracorporeal blood at a same point of time x or during a same time interval y.

The blood present in the extracorporeal blood circuit after a blood treatment session is removed from the extracorporeal blood circuit and may be discarded.

Although various passages in the present description make reference to a treatment apparatus for a dialysis treatment such as, for example, a hemodialysis, the present invention is in no way restricted to the performance of the method of removing blood from an extracorporeal blood circuit following a dialysis treatment.

Rather, the method of the invention is suited for removing or displacing blood from any extracorporeal blood circuit as known for the use in a multiplicity of extracorporeal blood treatments or in any extracorporeal blood treatment.

The extracorporeal blood circuit may preferably be connected to the patient's vascular system by means of so-called double-needle access or by means of so-called single-needle access.

A "double-needle access" to a patient's vascular system should be understood to be a form of connection wherein an arterial connection needle and a venous connection needle are each connected to the patient's vascular system and to the extracorporeal blood circuit, i.e., the arterial or venous portion thereof.

Although the present description is described exemplarily by way of a double-needle access, it is not restricted to such a realization.

The method of the invention may likewise be carried out by using a single-needle access. In this case, blood recirculated from the arterial conduit portion and from the venous conduit portion towards the single needle for connection to the patient may concurrently meet in a "Y"-shaped branching.

For this purpose, the "Y"-shaped branch or junction and/or the connection needle to the patient's vascular system may suitably be provided or configured, for example, by using suitable dimensions of the component's cross-sections and/or by the provision of flow-calming elements, flow guide elements, or the like.

In a preferred embodiment, blood is conveyed from the extracorporeal blood circuit by concurrently operating the blood pump and the second conveying means.

In a preferred manner, the blood may be conveyed both concurrently and with the same relative progress, both from the arterial conduit portion and from the venous conduit portion of the extracorporeal blood circuit.

The blood may, however, alternatively be conveyed concurrently but with a different relative progress both from the arterial conduit portion and from the venous conduit portion of the extracorporeal blood circuit.

The expression (relative) "progress" may here refer to the movement, or advance, of the blood, e.g., of a portion of blood, a blood front, and the like in a conduit portion (in the arterial or venous conduit portion) of the extracorporeal blood circuit relative to the patient or an access to the patient's vascular system.

The expression "relative" designates the advance of the blood in relation to the length of the respective conduit portion of the extracorporeal blood circuit to be passed through. In other words, the advance of the blood in the arterial conduit portion and in the venous conduit portion in a relative view may, for example, take place at a same velocity. As one conduit portion may be configured to be longer, have a larger diameter, include branchings, etc. in comparison with the other conduit portion, the relative advance does accordingly not correspond to the absolute advance, for instance with regard to accurate indications in terms of volume or centimeters. The advance may, for example, rather be indicated as a percentage of a conduit portion already emptied of blood or of a conduit portion still having to be emptied of blood.

An advance of the blood at the same velocity in differently configured conduit portions may, for example, be obtained by means of different rotation speeds of the conveying means. The advance at the same velocity may, for example, also be obtained by means of the quantity and the position of the addition site of the substituate liquid, and the like.

In a further preferred embodiment, the arterial conduit portion and/or the venous conduit portion of the extracorporeal blood circuit may be connected to a patient during the performance of the method.

Such a connection may—as is indicated in the foregoing—be realized in the form of double-needle or single-needle access.

In a preferred manner, the blood displaced from the extracorporeal blood circuit may substantially or completely be recirculated to the patient's vascular system. E.g., in the case of a single-needle access the blood may be reintroduced, or recirculated, to the patient's vascular system via a common access.

In another preferred embodiment of the method of the invention, the blood is conveyed until a phase boundary or a region of mixing between blood and substituate liquid reaches a detection means which is arranged in or on a portion of the extracorporeal blood circuit of the treatment apparatus.

The detection means may preferably be configured and intended for detecting a qualitative change of the contents of the (conduit interior of the) extracorporeal blood circuit.

A "detection means" may, e.g., be a—preferably optical—sensor which detects a change—e.g., an optical change—of the contents of the conduit interior or of a property of these contents.

The method of the invention may preferably be terminated as soon as the detection means recognizes, for example, the appearance of the phase boundary or of the mixing region of blood and substituate liquid.

In a particularly preferred manner, at least two detection means which may be configured identically or differently are arranged in the extracorporeal blood circuit. In particular, it may be advantageous to arrange a first detection means in the arterial conduit portion and a second detection means in the venous conduit portion. The two detection means may, for example, be arranged and provided at such a distance from the respective patient access, for instance from the arterial connection needle or from the venous connection needle, that blood has already been returned substantially completely from the extracorporeal blood circuit into the patient's vascular system when the detection means recognizes the appearance of a phase boundary or of a mixing region of blood and substituate liquid.

In a further preferred embodiment of the method of the invention, the conveying capacity or the conveying rate of the blood pump is controlled or regulated under consideration of at least one parameter relating to the extracorporeal blood circuit and/or a conveying capacity or a conveying rate of the second conveying means.

The conveying capacity or conveying rate of the blood pump may be adjusted, for example, by controlling or regulating a rotational speed of the blood pump.

The conveying capacity or the conveying rate of the second conveying means may correspond to a predetermined value or predetermined values and may, for example, be deposited and read out in a suitable means in or at the extracorporeal blood circuit and/or detected continuously and be utilized—preferably in real time—for a dynamic control or regulation of the conveying capacity or conveying rate of the blood pump.

As an alternative, or in supplementation thereto, it is provided in a further embodiment in accordance with the invention, to control or regulate a conveying capacity or a conveying rate of the second conveying means under consideration of at least one parameter relating to the extracorporeal blood circuit and/or a conveying capacity or a conveying rate of the blood pump. A control or regulation of the second conveying means or of a conveying capacity or conveying rate thereof may be carried out in analogy with the manner of proceeding indicated above.

The expression "parameter" as presently used may be understood to be a quantity and/or property that may be associated with a component of the extracorporeal blood circuit and/or with the second conveying means, for example a volume, e.g., the volume or the length of the conduit interior of a conduit portion of the extracorporeal blood circuit, a conveying rate of the second conveying means, a velocity, a conveying direction, and the like.

In a further preferred embodiment, a predetermined quantity of substitute liquid is introduced into the conduit interior of the extracorporeal blood circuit by operating the second conveying means.

A "predetermined quantity of substitute liquid or a predetermined amount of substitute liquid" may correspond to a particular conveying volume and/or a particular conveying distance of the blood to be conveyed or to be displaced along the conduit interior of the extracorporeal blood circuit. The introduction of a predetermined quantity of substitute liquid may, for example, take place by operating a membrane pump capable of highly accurate proportioning.

The quantity of substitute liquid may preferably be deposited and/or input, for example, in a control means.

In a further preferred embodiment of the method of the invention, recognition of air takes place by means of an air recognition detector or ABD (air bubble detector) as known from the prior art and as will furthermore be explained in the following, which is inserted in an arterial leg or conduit portion of an extracorporeal blood circuit or of a tube set. It should be noted that the expression "air" is presently not intended to have a restricting meaning. The present invention equally relates to any kind of gas.

Upon recognition of air in the arterial conduit portion a warning may be emitted. Independently of this, blood conveyance may be halted and/or further measures may be taken.

In this situation it is in particular possible to remedy the fault having resulted in an infusion of air, whether automatically or by personnel or by the user, respectively. The warning may be overruled in order to resume conveyance.

In this way, the quantity of air having entered and of the possibly generated blood foam volume may advantageously be minimized by quick intervention.

As an alternative, or in supplementation thereto, upon recognition of an inclusion of air or upon emission of a warning due to a recognized inclusion of air, a removal of air may take place in the arterial conduit portion, hereinafter also referred to an arterial removal of air. The method employed in this case may be the same as for a venous removal of air.

The arterial removal of air may differ in its application for on-line treatment and standard treatment:

In the case of an on-line treatment, the patient is disconnected arterially, and instead of the patient an external container, e.g. a NaCl bag, is coupled to the arterial patient tube. Subsequently—preferably following corresponding safety polling—substitute is conveyed from the hydraulic system—or from some other source—preferably via the pre-dilution valve into the arterial conduit portion of the tube system with the aid of the substitute pump. This is carried out in such a manner that the air present there is displaced into the connected container, which is also represented in FIG. 3. Once the tube system is free from air, the container is disconnected and the patient is again connected to the arterial patient tube or conduit portion. In this way, air does not enter and/or remain in the extracorporeal blood system.

I. a. in a HD (hemodialysis) treatment a removal of air may nevertheless also take place in the following manner: Upon recognition of an inclusion of air, the patient is disconnected both arterially and venously. Both patient tubes or conduit portions are connected to a container—preferably the above-mentioned NaCl bag—or to different containers. Subsequently—preferably following previous safety pollings—a content of the container, e.g. NaCl, is sucked into the venous blood tube system or into the venous conduit portion by reverse conveying on the part of the blood pump, whereby the air present in the arterial patient tube is conveyed into the container. If the user or a corresponding means recognizes that the tubing system is free from air (one option in this regard is an additional check of the venous branch or leg), the container is disconnected and the patient is again connected to the patient tubes. In this case, the air equally does not enter and/or remain in the extracorporeal blood system.

Apart from the two last ones of the above-described methods, which may also be referred to as "cautioning functions for arterially induced air", a method of the invention for safe reverse conveying in the extracorporeal system may also be performed by using at least one air recognition detector (in the following also in short: ABD). By this method a safe reverse conveying of blood by means of the blood pump is advantageously also possible in the connected state of the patient.

If the ABD and the corresponding control recognize arterial air in the process, an arterial air alarm is triggered. The latter may result or consist in immediate closing of the arterial patient tube clamp and/or stopping of blood conveyance. The removal of air may then take place as described above. As an alternative, the direction of flow may be reversed. In this way, the air may advantageously be discharged via the venous drip chamber.

In a preferred manner an additional examination is performed here by means of ABD and the corresponding control to ensure that no air is present in the respective tube portion. In this way an infusion of air into the patient is advantageously avoided.

Here, the following method may be employed: If a flow reversal is requested by the user (or automatically), a defined volume (preferably at least the volume of the blood system as far as behind the respective ABD) is initially conveyed further in the previous conveying direction while the air alert is activated, before the actual reversal of the direction of flow takes place or is initiated, respectively. Preferably such reversal is to be admissible only if the entire previous volume was conveyed without an air alert. In a preferred manner, the user has no possibility of manipulation or intervention between air alert and reversal of the direction of flow. By means of the method explained above, a fistula flow may advantageously also be determined.

The ABD inserted in the arterial leg further allows a so-called concurrent reinfusion, as will be described in the following. Here, the option of switching over the introduction of substitute between pre- and post-dilution without any additional action on the part of the user, such as reconnection of the connector and the like, shall be preferred.

During the concurrent reinfusion both connection needles remain in the patient's vascular system. In the venous part of the tube system the blood is displaced by conveying substitute via the pre-dilution port until the venous optical detector does not detect blood any more.

In a preferred manner, the blood pump should concurrently operate in the reverse direction. Here, the blood pump may preferably operate at a very low rate or speed.

As a result, a part of the substitute is conveyed into the arterial part of the system and there also displaces the blood towards the patient. Both ABDs are active. As it is a matter of comparatively small or very small volumes, arterial conveyance may be stopped by way of volume control. In a preferred manner, an optical sensor (OD) contained in the ABD may be used for this purpose.

In this method, it is possible to preferably only stop the blood pump upon occurrence of an arterial air alert. Venous reinfusion may be continued. A blood loss which then has to be accepted in a given case is less than 30 ml and thus negligible, or does not result in a significant impairment of the patient or of the patient's condition.

In certain embodiments of the method according to the invention, the blood return or reinfusion, respectively, of blood present in the extracorporeal blood circuit after termination of the blood treatment through the arterial patient line or the arterial line section, respectively, or arterial leg comprises the use of a clot trap. According to the present invention, the clot trap is or will be arranged such that it allows a through-flow of blood which is returned to the patient through the arterial patient line or is removed from the extracorporeal blood circuit in any other way.

In some embodiments according to the invention, the clot trap can be inserted manually in a corresponding blood-conducting arterial section of the extracorporeal blood circuit. It can, for example, be inserted between a section of the arterial line section and the arterial connection needle. The clot trap can, for example, be inserted between an, in particular originally present, tube end of the arterial line section and an, in particular originally present, end of the flexible tube section of the arterial connection needle, for example, after a simple common disconnecting of the arterial line section form the flexible tube section of the arterial connection needle. In certain embodiments according to the invention, the clot trap is inserted after termination of the blood treatment.

In some embodiments according to the invention, the use of the clot trap comprises one or more of the following steps:
a) The clot trap which optionally has to be taken from a sterile packaging is filled with an appropriate liquid, preferably a saline solution, if this is not already the case yet.
b) The reinfusion and/or the blood conveyance by means of the blood pump is interrupted by correspondingly controlling the treatment apparatus. In some embodiments according to the invention, this is effected by actuating a soft key of the treatment apparatus.
c) At the arterial line section and at the tube line of the arterial connection needle (or in the range or space thereof, respectively), the blood flow is stopped, preferably by means of two patient tube clamps. Hereupon, the tube line of the arterial connection needle and the arterial line section can be separated from each other.
d) The clot trap is connected with the tube line of the arterial connection needle.
e) The clot trap is connected with the arterial line section.
f) If provided, both patient tube clamps (one at the tube line of the arterial connection needle and one at the arterial line section) are opened. In either case, the interrupted blood flow is recovered or re-established, respectively.
g) The reinfusion and/or the blood conveyance by means of the blood pump having temporarily been stopped is started again. This can, for example, be effected by actuating a soft key at the treatment apparatus.
h) By means of the treatment apparatus, in some embodiments according to the invention, a, preferably predetermined, volume is sucked or aspirated, respectively, through the arterial line section at first. In certain embodiments according to the invention, the simultaneous reinfusion and contemporary return through both of the line sections or patient lines, respectively, will only be started thereafter.

The order of the afore-mentioned steps a) to h) can be varied arbitrarily as long as a person skilled in the art recognizes the feasibility thereof.

In certain embodiments of the invention described herein, the clot trap according to the invention includes a mesh size of preferably 10 to 200 micrometers (µm) as well as any number in between. In some embodiments according to the invention, the mesh size is 40 or 160 micrometers (µm).

The advantages achievable with the method of the invention may also be achieved in an undiminished manner with the treatment apparatus of the invention.

The treatment apparatus of the invention comprises at least one extracorporeal blood circuit including an arterial conduit portion and a venous conduit portion, at least one conveying means for introducing and/or conveying a fluid in the extracorporeal blood circuit, as well as at least one control or regulating means suited and intended for performing or operating, or controlling or regulating, the method of the invention.

The "conveying means" for introducing and/or conveying a fluid into or within the extracorporeal blood circuit encompasses a blood pump for conveying blood within the conduit interior of the extracorporeal blood circuit arranged at or in the extracorporeal blood circuit. The "blood pump" may be implemented, e.g., as a peristaltic pump, a hose pump, a roller pump or any other suitable pump.

The treatment apparatus of the invention further comprises at least one second conveying means for introducing at least one substitute liquid into the conduit interior of the extracorporeal blood circuit for its conveyance inside the conduit interior. The second conveying means may be a peristaltic pump, e.g., a hose pump or a roller pump. It is, however, also possible to employ some other pump type, e.g. a membrane pump, in particular a membrane pump capable of highly accurate proportioning.

The second conveying means may comprise feed conduits, for example a substitute liquid feed conduit, towards various storage means such as substitute liquid storage means or storage containers with substitute liquid.

The second conveying means may further comprise at least one control or regulating means which enables, while also being intended for this purpose, an automated introduction and/or conveyance of the at least one substitute liquid, for example of a predetermined quantity of substituate liquid.

The second conveying means together with its components, in particular its feed conduits in the extracorporeal blood circuit, preferably represents a part of the tube set or tube system for the extracorporeal blood treatment. It may be provided at or in the extracorporeal blood circuit. It may in particular be connected to the latter in a suitable manner, for example with the aid of clamps, branch necks, or the like.

The second conveying means may alternatively also be situated within the extracorporeal blood circuit. The second conveying means may suck in substitute liquid, e.g., via the substitute liquid feed conduit.

A substitute conduit or substitute liquid feed conduit is preferably a feed conduit which may be connected from a substitute source or substitute liquid supply means. The substitute conduit may be a component part or accessory part of a tube set for the extracorporeal blood treatment. It may, however, also be configured such as not directly being a component part of the extracorporeal blood circuit, in the sense that no blood flows through the substitute conduit.

The treatment apparatus of the invention may further comprise, for example, a treatment apparatus for treating the patient's blood, such as one or several blood filter(s) and/or one or several dialyzer(s), for example a hemodialyzer, and/or one or several absorption means or adsorption means.

The treatment apparatus may furthermore also comprise containers for storing fluids, elements for introducing the fluids such as, for example, tube elements and/or valves, as well as additional means such as, e.g., a drip chamber for removing air from the blood during the blood treatment and/or sensors and/or detectors for detecting different relevant parameters such as, for example, a pressure in the extracorporeal blood circuit.

The single components may be interconnected in a differential design, i.e., the components may be joined together additively by joining technology, e.g., by bonding and/or welding such as plastic welding or laser welding. The components may be part of an external functional means such as, for example, a blood cassette. Such a blood cassette is disclosed, for instance, in the German Patent Application Nos. 10 2009 018 664.6 and 10 2009 024 468.9 each having the title "Externe Funktionseinrichtung, Blutbehandlungsvorrichtung zum Aufnehmen ether erfindungsgemäßen Funktionseinrichtung, sowie Verfahren" [External functional means, blood treatment apparatus for receiving an external functional means in accordance with the invention, and method] as deposited by the applicant of the present invention with the German Patent and Trademark Office on Apr. 23, 2009 and on Jun. 10, 2009, respectively, the respective disclosures of which are herewith fully incorporated by way of reference.

The treatment apparatus of the invention may comprise at least one such external functional means preferably having the form of such a blood cassette.

Single components of a treatment apparatus in accordance with the present invention may correspond to the embodiments disclosed in the German Patent Application No. 10 2009 008 346.4 having the title "Verfahren zum Entfernen von Blut aus einem extrakorporalen Blutkreislauf für eine Behandlungsvorrichtung nach Beenden ether Blutbehandlungssitzung and Vorrichtung zum Ausführen desselben" [Method of removing blood from an extracorporeal blood circulation for a treatment apparatus following termination of a blood treatment session, and apparatus for performing said method] as deposited by the applicant of the present invention with the German Patent and Trademark Office on Feb. 11, 2009, for which reason the relevant disclosure thereof is herewith fully incorporated by way of reference.

In a preferred embodiment, the treatment apparatus comprises at least one control or regulating means suited and intended (i.e., configured) to control or regulate a conveying capacity or a conveying rate of the blood pump and/or of the second conveying means under consideration of at least one parameter relating to the extracorporeal blood circuit.

The parameter, for example data or information in the form of characteristic quantities or properties relating to the extracorporeal blood circuit, may be selected from parameters relating to an internal volume of the arterial conduit portion of the extracorporeal blood circuit, parameters relating to an internal volume of the venous conduit portion of the extracorporeal blood circuit, parameters relating to an addition site for the substitute liquid, such as the position of a pre-dilution addition site for the substitute liquid and/or the position of a post-dilution addition site for the substitute liquid, and/or parameters relating to the conveying capacity or conveying rate of the second conveying means, however without being restricted to the above-mentioned examples.

In another preferred embodiment, the treatment apparatus may comprise at least one memory means in which the parameter relating to the extracorporeal blood circuit may be stored or deposited.

The "memory means" may be a permanently provided memory means such as, for example, a hard disc, and/or an external memory means such as a CD, a diskette, an SD card or SD Memory Card (Secure Digital Memory Card), and the like.

The treatment apparatus may comprise at least one input means by means of which the parameter may be deposited in a memory means.

Such an "input means" may be a keyboard, a touch pad, a touch-screen, a microphone, a reading unit, and the like.

Inputting the parameter may be carried out by a user, for instance manually by typing on a keyboard. Depositing the parameter in the memory means may also be carried out by means of transmission from an external data carrier and/or another memory means, for example via an IR interface, Bluetooth, a USB port, Firewire, SATA, and the like to the treatment apparatus.

Following inputting or deposition of the parameter in the memory means, the parameter may be stored permanently. It may, however, also only be deposited for the duration of one treatment session and be stored temporarily, for example.

In another preferred embodiment, the memory means is suited and intended, or configured, for storing parameters of various and furthermore different extracorporeal blood circuits. The data stored for the tube system or the blood tube set utilized in a treatment session may, for example, be selected prior to the beginning of a treatment.

This may in particular be advantageous if various or different kinds or systems or arrangements of extracorporeal blood circuits or of tube systems are to be employed in or on a treatment apparatus.

In a further preferred embodiment, the memory means may be provided at or in at least one portion of the extracorporeal blood circuit. For instance, the memory means may be realized as a barcode and/or a 2D-Code (Dot-Matrix-Code) and/or a RFID chip. Thus the treatment apparatus may read in the data or parameters, for example automatically, and provide them to the control or regulating means. It may be provided, for example, at the tube system, e.g., at the arterial and/or venous conduit portion of the extracorporeal blood circuit.

The memory means may be provided at or in an external functional means such as, for example, the blood cassette mentioned in the foregoing. For example, the specifications of the single components or portions of the blood cassette determined during manufacture of the blood cassette may in such a case be deposited in the memory means.

When the memory means is provided as an external memory means, the treatment apparatus may preferably further comprise at least one reception means and/or at least one reading unit suited and intended for receiving and reading out the external memory means.

The "reception means" may, for instance, be a card reader, a slot for receiving a SD card or a diskette, a tray for receiving a CD, and the like. The parameters or data or information deposited on the memory means may be read out or read after introducing or entering or inserting the memory means into the reception means. This may take place by means of a reading unit such as, for example, a laser.

The "reading unit" may also be an external means or a free-standing means of the treatment apparatus such as, for example, a scanner. Introducing or inserting or entering the memory means into a reception means is thus not required. The parameters or data or information items may be read out or read simply by arranging or touching the memory means in front of the reading unit.

A suitable external memory means may, for example, also be provided in or on a patient card having, for example, the form of a chip.

The read-out or read parameters may be transmitted to a central processor of a control or regulating means of the treatment apparatus and used, for example, for controlling or regulating the conveying capacity or conveying rate of the blood pump.

The object of the invention is furthermore also achieved through a tube system that is suited for use in a method of the invention or for use with a treatment apparatus of the invention. The advantages achievable with the method of the invention may also be achieved in an undiminished manner with the tube system of the invention.

The tube system of the invention comprises at least one memory means in or from which parameters relating to the tube system and/or an extracorporeal blood circuit may be read.

The tube system may be part of an extracorporeal blood circuit. It may, for example, comprise the arterial conduit portion and/or the venous conduit portion of the extracorporeal blood circuit or constitute these. The tube system may, for example, be made of conventional plastic material.

The tube system of the invention and/or the treatment apparatus of the invention (e.g., the dialysis apparatus) preferably comprises at least one ABD (air bubble detector). The latter may be provided in the arterial conduit portion or leg and/or in the venous conduit portion of the tube system. The ABD may have a configuration as disclosed in EP 1 952 832 A1, the relevant disclosure of which is herein incorporated by way of reference.

By means of the method of the invention, it is advantageously possible to speedily remove blood, which is present in an extracorporeal blood circuit of a treatment apparatus following termination of a blood treatment session, both from the arterial conduit portion and from the venous conduit portion of the extracorporeal blood circuit.

Thereby, in certain embodiments according to the invention, an increased safety can be offered to the patient. In particular, a clot displacement or carryover, respectively, into the patient's vascular system can be prevented. At least, the risk for such a displacement can be reduced.

By means of the control means and on the basis of the data of the internal volumes of all or some portions of the blood tube set, in a given case under consideration of the position of the selected addition site or inlet site for the substituate and/or the predetermined conveying rate or conveying capacity of the substituate pump, the treatment apparatus of the invention may be capable of automatically calculating the required conveying rate or the required conveying capacity of the blood pump or of some other conveying means in such a manner, and to correspondingly control the blood pump or other conveying means such that a simultaneous displacement of the blood from the—generally different—volumes of the arterial and venous conduit portions in the patient may take place.

In a particularly advantageous manner, the blood pump or some other conveying means may be controlled such that returning the blood may take place not only concurrently but also at the same velocity. In accordance with the invention it may thus advantageously be possible to concurrently terminate the removal of the blood from two conduit portions of the extracorporeal blood circuit. In this way, time and costs may be saved in a particularly advantageous manner.

As the blood may be recirculated concurrently and at the same progress from the two conduit portions into the patient's vascular system, an unnecessary or inadvertent infusion of substituate liquid after termination of the blood treatment into the patient's vascular system may advantageously be avoided.

Due to the possibility of removing the blood substantially entirely from the extracorporeal blood circuit and concurrently rinsing the extracorporeal blood circuit with substituate liquid, the risk of a contamination of third persons or of the surroundings with patient's blood may advantageously be reduced. This is particularly true for the disposal of the extracorporeal blood circuit following termination of the treatment.

BRIEF DESCRIPTION OF THE DRAWINGS

In the following, the present invention shall be described by way of preferred embodiments thereof while making reference to the drawings. In the drawings, identical reference numerals designate same or identical elements, wherein.

DETAILED DESCRIPTION OF THE DRAWINGS

For the exemplary explanation of the present invention a blood treatment apparatus, for example a hemodialyzing apparatus, is selected as a treatment apparatus, and a blood treatment method, for example a hemodialysis, is selected as a method. It is expressly noted that emptying the extracorporeal blood circuit may also take place in accordance with the invention without the removed blood being recirculated to the patient.

Figure 2:
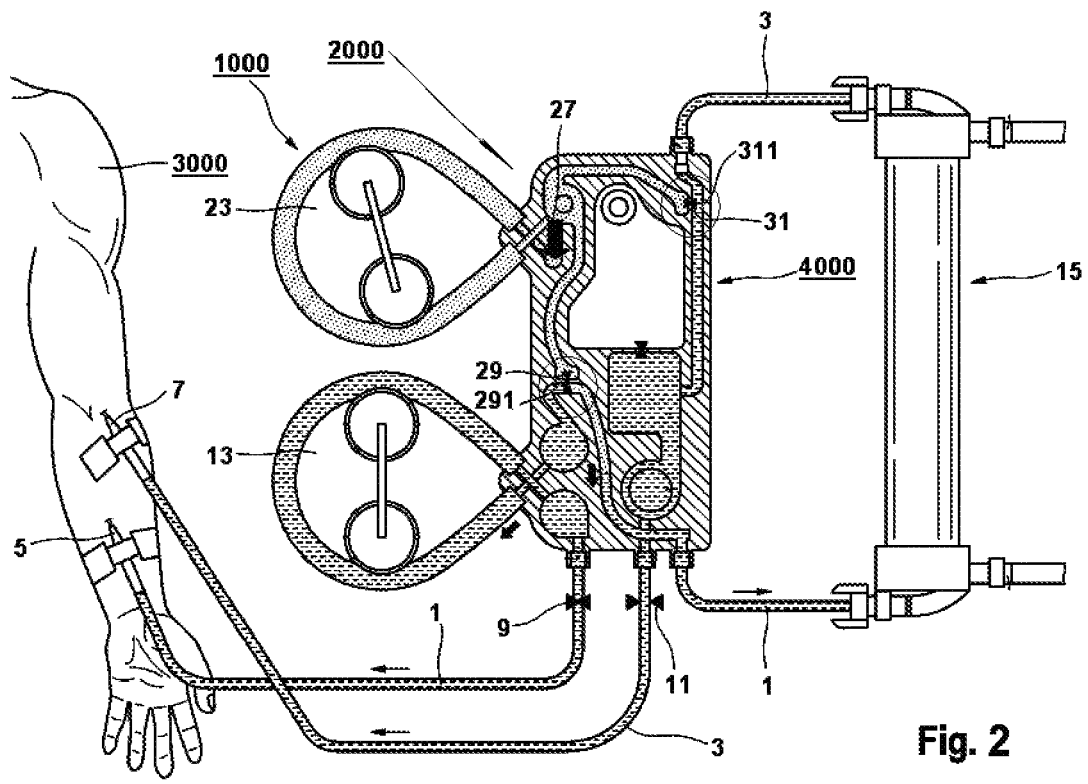
FIG. 2 shows in a schematically simplified manner a phase during the performance of a method of the invention.

The standard arrows in FIG. 2 indicate a direction of the blood stream. The block arrows each indicate one direction of the substituate stream.

Figure 1:
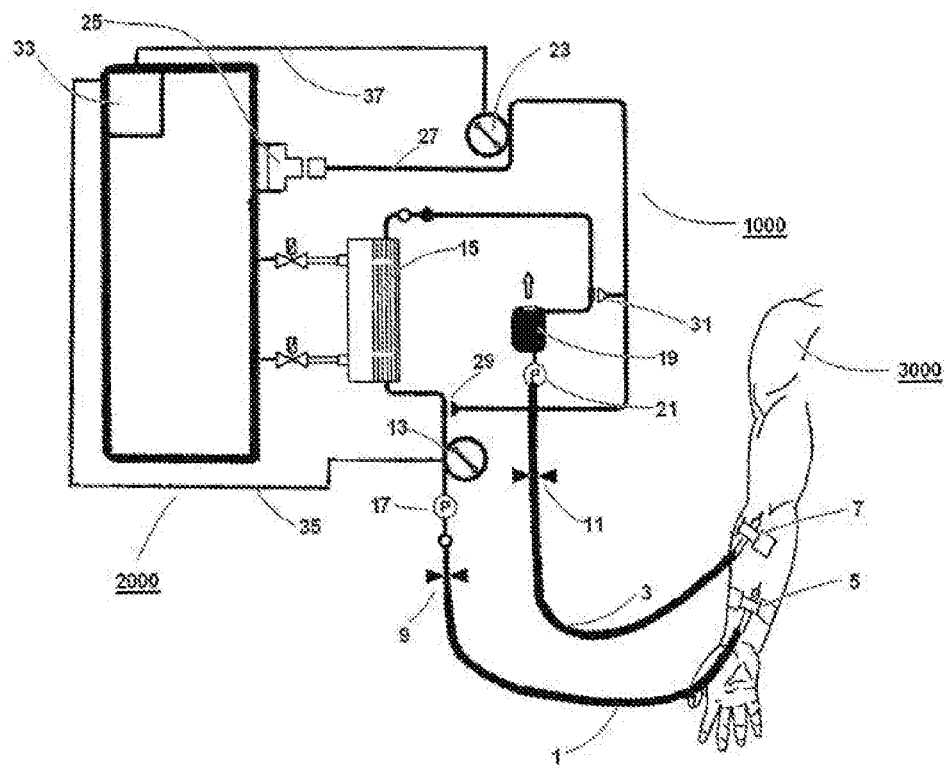
FIG. 1 shows a schematic overview of an exemplary treatment apparatus of the invention for performing the method of the invention.

In FIG. 1 an extracorporeal blood circuit 1000 of a treatment apparatus 2000 of the invention having a double-needle access to the vascular system of a patient 3000 is represented. The extracorporeal blood circuit 1000 comprises an arterial conduit portion 1 as well as a venous conduit portion 3.

The arterial conduit portion 1 is connected via an arterial patient access, for example as shown in FIG. 1 and having the form of an arterial connection needle 5, to the vascular system of the patient 3000. The venous conduit portion 3 is connected via a venous patient access, for example as shown in FIG. 1 and having the form of a venous connection needle 7, to the vascular system of the patient 3000.

The arterial conduit portion 1 comprises an arterial patient tube clamp 9; the venous conduit portion 3 comprises a venous patient tube clamp 11. In FIG. 1 both the arterial patient tube clamp 9 and the venous patient tube clamp 11 are represented in an opened, or open, state.

The extracorporeal blood circuit 1000 comprises a blood pump 13. The blood pump 13 is exemplarily configured as a roller pump. The blood pump 13 conveys blood of the patient 3000 through the extracorporeal blood circuit 1000.

The extracorporeal blood circuit 1000 comprises a blood treatment means 15, for example a hemodialyzer.

As is shown in FIG. 1, an arterial pressure sensor 17 is arranged in the arterial conduit portion 1 downstream (relative to the conveying direction that is usual during a blood treatment) from the blood pump 13. In the venous conduit portion 3 a venous drip chamber 19 and a venous pressure sensor 21 upstream from the venous drip chamber 19 are arranged.

By means of a second conveying means, for example a substitute pump 23, substitute liquid may be introduced into the extracorporeal blood circuit 1000 from a substitute liquid supply means 25 via a substitute liquid feed conduit 27 at a pre-dilution addition site 29 for substitute liquid and/or a post-dilution addition site 31 for substitute liquid. The substitute pump 23 is here exemplarily configured as a roller pump.

The treatment apparatus 2000 comprises a regulating or control means 33. The control means 33 is connected via a control line 35 to the blood pump 13 and via a control line 37 to the substitute pump 23. It may, however, be sufficient to provide only one regulating or control line, optionally to the blood pump 13 or to the substitute pump 23, in order to perform the method of the invention.

The control means 33 may, for example, control a conveying rate or a conveying capacity of the blood pump 13 as a function of operating parameters of the substitute pump 23, e.g., the conveying rate or conveying capacity thereof. The control lines 35 and 37 may admit a bidirectional communication between the control means 33 and the blood pump 13 or the substitute pump 23, respectively.

FIG. 1 shows a connection of the blood treatment apparatus 2000 of the invention to the patient's vascular system. Such a connection is, however, not indispensable for realizing the blood treatment apparatus of the invention but only represents a particular realization and a preferred utilization.

In FIG. 2 the treatment apparatus 2000 comprises an external functional means such as, for example, a blood cassette 4000. The blood cassette 4000 may be a blood cassette as disclosed in the German Patent Application No. 10 2009 018 664.6 and German Patent Application No. 10 2009 024 468.9. each having the title "Externe Funktionseinrichtung, Blutbehandlungsvorrichtung zum Aufnehmen ether erfindungsgemäßen externen Funktionseinrichtung, sowie Verfahren" [External functional means, blood treatment apparatus for receiving an external functional means in accordance with the invention, and method] that were deposited by the applicant of the present invention with the German Patent and Trademark Office on Apr. 23, 2009 and on Jun. 10, 2009, see above; the respective disclosures of which are herewith in turn fully incorporated by way of reference.

FIG. 2 shows a phase of a method of the invention for removing blood from the extracorporeal blood circuit 1000 following termination of a blood treatment in a particular embodiment in which the blood is recirculated into the patient's vascular system. Both the arterial patient tube clamp 9 and also the venous patient tube clamp 11 are in an opened, or open, state.

The blood pump 13 and the substitute pump 23 are operated. In the following, the expressions "clockwise" or "counter-clockwise" refer to the plane of drawing of FIG. 2. They are intended to indicate the conveying direction of the pumps during a dialysis treatment and during the method of the invention: During a blood treatment process, the blood pump 13 and the substitute pump 23 usually convey in a counter-clockwise direction as might be seen from FIG. 2.

During the performance of the method of the invention, the blood pump 13 rotates in the clockwise direction and thus against the conveying direction that is usual during a blood treatment (patient—arterial conduit portion—blood treatment means—venous conduit portion—patient).

The substitute pump 23 rotates in the counter-clockwise direction.

The rotational speeds of the blood pump 13 and of the substitute pump 23 may be different from each other. The rotation speeds of blood pump 13 and substitute pump 23 may be identical. The blood pump 13 and the substitute pump 23 may be started at a same point of time and/or made to rotate for a same (predetermined) time period. The blood pump 13 and the substitute pump 23 may be made to rotate at different points of time and/or for different (predetermined) time periods.

Blood is present in the extracorporeal blood circuit 1000 (simple-hatching area). Substitute liquid is introduced via the substitute liquid feed conduit 27 (cross-hatched area in FIG. 2).

A pre-dilution addition valve 291 of the pre-dilution addition site 29 is opened. As an alternative, or in addition, a post-dilution addition valve 311 of the post-dilution addition site 31 may also be opened. In the representation shown in FIG. 2, the post-dilution addition valve 311 of the post-dilution addition site 31 is, however, closed.

The pre-dilution addition valve 291 and the post-dilution addition valve 311 may, for example, be configured as so-called phantom valves as disclosed in the above-mentioned applications to the present applicant having the title "Externe Funktionseinrichtung, Blutbehandlungsvorrichtung zum Aufnehmen einer erfindungsgemäßen externen Funktionseinrichtung, sowie Verfahren" [External functional means, blood treatment apparatus for receiving an external functional means in accordance with the invention, and method] as well as in the German Patent Application No. 10 2009 012 632.5 having the title "Abdichtungseinrichtung zum Abdichten eines Volumens ether medizinischen Behandlungsanordnung gegen ein weiteres Volumen sowie Anordnung and Verfahren" [Sealing means for sealing a volume of a medical treatment arrangement against another volume, as well as arrangement and method] as filed with the German Patent and Trademark Office on Mar. 10, 2009, the relevant disclosure of which is herewith fully incorporated by way of reference.

Substitute liquid may enter the extracorporeal blood circuit 1000 via the pre-dilution addition valve 291.

FIG. 2 shows a momentary status of configuration of the blood treatment apparatus 2000 during the blood emptying or blood recirculation process, wherein the substituate liquid is introduced into the extracorporeal blood circuit 1000 at an upstream position (relative to the conveying direction that is usual during a blood treatment) through the opened pre-dilution addition valve 291.

The substituate liquid may displace the blood between the pre-dilution addition valve 291 and the venous connection needle 7, i.e., the blood present upstream from the pre-dilution addition valve 291 in the arterial conduit portion 1 and the blood present in the venous conduit portion 3.

The displaced blood may be recirculated through the venous connection needle 7 into the patient's vascular system.

The substituate liquid is conveyed through the arterial conduit portion 1 of the extracorporeal blood circuit 1000 upstream from the pre-dilution addition valve 291 through the treatment means 15 and the venous conduit portion 3 towards the patient 3000.

At the same time, the blood present in the extracorporeal blood circuit 1000 in front of or downstream from the pre-dilution addition valve 291 in the conveying direction is conveyed through the arterial conduit portion 1 to the patient 3000.

Here, the substituate liquid is introduced from the pre-dilution addition valve 291 into the arterial conduit portion 1 arranged downstream from the pre-dilution addition valve 291 and conveyed in the direction towards the patient 3000.

The simultaneous emptying of blood from the arterial conduit portion 1 of the extracorporeal blood circuit 1000 and from the venous conduit portion 3 of the extracorporeal blood circuit 1000 may in the preferred manner take place with the same progress, i.e., the degree or extent of emptying (e.g., in percent of a conduit content) of the blood still present in the respective conduit portions 1 and 3 may be identical at any point of time.

Emptying or recirculation of the blood from the extracorporeal blood circuit 1000 may be terminated concurrently. For example, the blood pump 13 and the substituate pump 23 may be stopped shortly before the substituate liquid reaches the arterial connection needle 5, and correspondingly shortly before the substituate liquid reaches the venous connection needle 7.

As an alternative, the substituate liquid may—as was already mentioned in the foregoing—also or additionally also be introduced into the extracorporeal blood circuit 1000 via the post-dilution addition valve 311.

The performance of the method of the invention does, however, substantially correspond to the manner of proceeding indicated in the foregoing for the substituate liquid supplied by means of pre-dilution, so that reference is here made to these above explanations.

Figure 3:
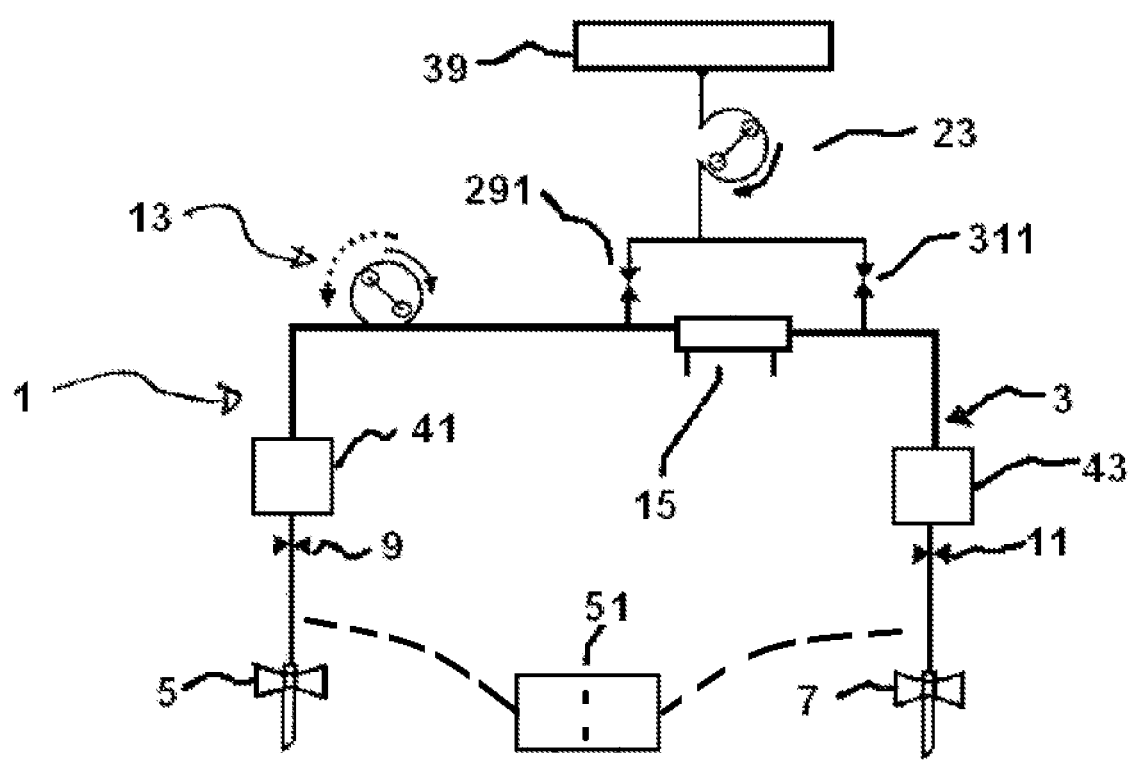
FIG. 3 shows a schematic diagram of an extracorporeal blood system including an arterial ABD (air bubble detector).

FIG. 3 shows a schematic diagram of an extracorporeal blood system including an arterial ABD (air bubble detector) or air-recognition detector for performing methods of the invention. The represented components are essentially already known from FIGS. 1 and 2. In comparison therewith, there are additionally only present a hydraulic system 39, an arterial ABD (air bubble detector) 41, a venous ABD 43, and a container 51.

The pumping directions indicated by arrows drawn in solid lines correspond to the regular directions, or forward directions. The pumping direction of the blood pump 13 indicated by dotted lines corresponds to its reverse operation, or suction by the blood pump 13.

List of Reference Numerals

| Reference Numeral | Description |
| --- | --- |
| 1000 | extracorporeal blood circuit |
| 2000 | treatment apparatus |
| 3000 | patient |
| 4000 | blood cassette |
| 1 | arterial conduit portion |
| 3 | venous conduit portion |
| 5 | arterial connection needle |
| 7 | venous connection needle |
| 9 | arterial patient tube clamp |
| 11 | venous patient tube clamp |
| 13 | blood pump |
| 15 | blood treatment means |
| 17 | arterial pressure sensor |
| 19 | venous drip chamber |
| 21 | venous pressure sensor |
| 23 | substituate pump |
| 25 | substituate liquid supply means |
| 27 | substituate liquid feed conduit |
| 29 | pre-dilution addition site |
| 291 | pre-dilution addition valve |
| 31 | post-dilution addition site |
| 311 | post-dilution addition valve |
| 33 | control means |
| 35 | control line to the blood pump |
| 37 | control line to the substituate pump |
| 39 | hydraulic system |
| 41 | arterial air recognition detector (ABD) |
| 43 | venous air recognition detector (ABD) |

We claim:

1. A method for at least one of recognizing and eliminating air inclusions in or from an extracorporeal blood circuit of a treatment apparatus, the method comprising:
 providing a treatment apparatus comprising:
  at least one device adapted to receive an extracorporeal blood circuit, the extracorporeal blood circuit including an arterial conduit portion and a venous conduit portion;
  at least one blood pump adapted to convey blood within the extracorporeal blood circuit;
  at least one conveyor adapted to at least one of (i) introduce at least one substituate liquid into the extracorporeal blood circuit and (ii) convey the substituate liquid within the extracorporeal blood circuit; and
  at least one arterial air detector;
 detecting, using the arterial air detector, air in the arterial conduit portion of the extracorporeal blood circuit;
 connecting the arterial conduit portion to a container; and
 conveying, by the conveyor, the substituate liquid from a hydraulic system into the arterial conduit portion while displacing the air from the arterial conduit portion into the container.

2. The method according to claim 1, further comprising: emitting, by the treatment apparatus, a warning in response to the detecting the air in the arterial conduit portion.

3. The method according to claim 1, further comprising: stopping, in response to the detecting the air in the arterial conduit portion, conveyance of blood by at least one of the blood pump and the conveyor.

4. The method according to claim 1, further comprising: performing safety pollings.

5. The method according to claim 1, further comprising: connecting the venous conduit portion to the container.

6. The method according to claim 5, further comprising:
reverse conveying, by the blood pump, contents of the extracorporeal blood circuit to convey the air present in the arterial conduit portion into the container.

7. The method according to claim 6, further comprising:
disconnecting the arterial and venous conduit portions from the container.

8. The method according to claim 1, further comprising:
at least one of (i) closing an arterial patient tube clamp of the treatment apparatus and (ii) stopping conveyance of the blood in response to the detecting of the air by the arterial air detector.

9. The method according to claim 8, further comprising:
stopping the conveyance of the blood.

10. The method according to claim 1, further comprising:
reversing a conveying direction of the blood pump.

11. The method according to claim 10, further comprising:
after reversing the conveying direction of the blood pump, detecting, by the arterial air detector, air in the extracorporeal blood circuit.

12. The method according to claim 10, further comprising:
conveying, by the blood pump and prior to the reversing the conveying direction of the blood pump, a predefined volume of liquid.

13. The method according to claim 12, further comprising:
determining, using the arterial air detector, whether the predefined volume was conveyed without air.

14. The method according to claim 1, further comprising:
suppressing an intervention by a user of the treatment apparatus during removal of the air from the extracorporeal blood circuit.

15. The method according to claim 1, wherein the extracorporeal blood circuit includes a clot trap in the arterial conduit portion.

16. The method according to claim 1, wherein the treatment apparatus comprises a dialyzing apparatus or a hemodialysis apparatus.

17. The method according to claim 1, wherein the substitute liquid conveyed from the hydraulic system into the arterial conduit portion by the conveyor is a predetermined quantity of the substitute liquid.

18. The method according to claim 1, further comprising:
conveying, by the blood pump, a predefined volume of liquid;
after conveying the predefined volume of the liquid, reversing a conveying direction of the blood pump; and
after reversing the conveying direction of the blood pump, detecting, by the arterial air detector, air in the extracorporeal blood circuit.

* * * * *